United States Patent
Gage et al.

(10) Patent No.: US 11,925,782 B2
(45) Date of Patent: Mar. 12, 2024

(54) APPARATUS AND METHOD FOR CANNULATION OF VASCULAR ACCESS VESSEL

(71) Applicant: InnAVasc Medical, Inc., Durham, NC (US)

(72) Inventors: Shawn M. Gage, Raleigh, NC (US); Joseph Knight, Durham, NC (US); Michael Lawson, Durham, NC (US); Craig Nichols, Carrboro, NC (US)

(73) Assignee: InnAVasc Medical, Inc., Durham, NC (US)

( * ) Notice: Subject to any disclaimer, the term of this patent is extended or adjusted under 35 U.S.C. 154(b) by 877 days.

(21) Appl. No.: 16/877,054

(22) Filed: May 18, 2020

(65) Prior Publication Data

US 2020/0276430 A1    Sep. 3, 2020

Related U.S. Application Data

(62) Division of application No. 16/175,698, filed on Oct. 30, 2018.

(51) Int. Cl.
  *A61M 39/02*  (2006.01)
  *A61M 1/30*  (2006.01)
  *A61M 1/36*  (2006.01)

(52) U.S. Cl.
  CPC .......... *A61M 39/0208* (2013.01); *A61M 1/30* (2013.01); *A61M 1/3655* (2013.01);
  (Continued)

(58) Field of Classification Search
  CPC .......... A61M 5/427; A61M 2039/0238; A61B 90/11
  See application file for complete search history.

(56) References Cited

U.S. PATENT DOCUMENTS 3,999,504 A    12/1976    Kearse
4,004,298 A    1/1977    Freed
(Continued)

FOREIGN PATENT DOCUMENTS

AU    2011100534 A4    6/2011
AU    2012229032 B2    6/2015
(Continued)

OTHER PUBLICATIONS

Gage, Shawn M.; Non-Final Office Action for U.S. Appl. No. 16/580,423, filed Sep. 24, 2019, dated Apr. 14, 2022, 17 pgs.
(Continued)

*Primary Examiner* — Courtney B Fredrickson

(57) ABSTRACT

A method for rotatable selection of sites for cannulation of a subcutaneous vascular access vessel comprises the step of providing a template defining an opening for a plurality of zones, each of the plurality of zones configured for receiving a plurality of simultaneous cannulations accessing the vascular access vessel. The outer surface of the template is marked, the marking defining each of the plurality of zones for use as cannulation sites along the vascular access vessel. The template is positioned on the skin of the patient adjacent the subcutaneous vascular access vessel such that the opening aligns with the vascular access vessel, and the marking is used for selecting a first zone for a cannulation site into the vascular access vessel such that the cannulation site in the first zone is spaced from and not adjacent to a second zone used for cannulation immediately previously to the first zone.

18 Claims, 11 Drawing Sheets

(52) U.S. Cl.
CPC ............... *A61M 2039/0238* (2013.01); *A61M 2205/583* (2013.01)

(56) References Cited

U.S. PATENT DOCUMENTS

| | | |
|---|---|---|
| 4,121,003 A | 10/1978 | Williams |
| 4,228,796 A | 10/1980 | Gardiner |
| 4,268,983 A | 5/1981 | Cook |
| 4,619,641 A | 10/1986 | Schanzer et al. |
| 4,642,096 A | 2/1987 | Katz |
| 4,723,544 A | 2/1988 | Moore et al. |
| 4,733,661 A | 3/1988 | Palestrant |
| 4,822,341 A | 4/1989 | Colone |
| 5,123,907 A | 6/1992 | Romaine |
| 5,147,307 A | 9/1992 | Gluck |
| 5,167,629 A | 12/1992 | Vertenstein et al. |
| 5,192,310 A | 3/1993 | Herweck et al. |
| 5,312,350 A | 5/1994 | Jacobs |
| 5,358,281 A | 10/1994 | Greig |
| 5,364,361 A | 11/1994 | Battenfield |
| 5,633,058 A | 5/1997 | Hoffer et al. |
| 5,700,287 A | 12/1997 | Myers et al. |
| 5,704,915 A | 1/1998 | Melsky et al. |
| 5,713,859 A | 2/1998 | Finch et al. |
| 5,849,036 A | 12/1998 | Zarate |
| 6,024,723 A | 2/2000 | Cota |
| 6,036,632 A | 3/2000 | Whitmore, III et al. |
| 6,102,884 A | 8/2000 | Squitieri |
| 6,146,414 A | 11/2000 | Gelman |
| 6,261,257 B1 | 7/2001 | Uflacker et al. |
| 6,283,942 B1 | 9/2001 | Staehlin et al. |
| 6,428,504 B1 | 8/2002 | Riaziat et al. |
| 6,500,109 B2 | 12/2002 | Tokita et al. |
| 6,508,786 B2 | 1/2003 | Huitema et al. |
| 6,547,820 B1 | 4/2003 | Staudenmeier |
| 6,626,865 B1 | 9/2003 | Prisell |
| 7,108,673 B1 | 9/2006 | Batiste |
| 7,261,705 B2 | 8/2007 | Edoga et al. |
| 7,452,374 B2 | 11/2008 | Hain et al. |
| 7,527,593 B2 | 5/2009 | Fidel et al. |
| 7,540,859 B2 | 6/2009 | Claude et al. |
| 7,566,317 B1 | 7/2009 | Batiste et al. |
| 7,670,333 B2 | 3/2010 | Schatzberger |
| 7,713,234 B2 * | 5/2010 | Karanzas ................ A61J 7/04 604/116 |
| 7,722,535 B2 | 5/2010 | Randlov et al. |
| 7,740,593 B2 | 6/2010 | Shabaz |
| 7,762,977 B2 | 7/2010 | Porter et al. |
| 7,780,622 B2 | 8/2010 | Fitzpatrick et al. |
| 7,780,662 B2 | 8/2010 | Bahney |
| 7,806,922 B2 | 10/2010 | Henderson et al. |
| 7,828,781 B2 | 11/2010 | Edoga et al. |
| 7,833,186 B1 | 11/2010 | Batiste |
| 8,029,563 B2 | 10/2011 | House et al. |
| 8,066,758 B2 | 11/2011 | Bogert et al. |
| 8,075,525 B2 | 12/2011 | Yang |
| 8,105,307 B2 | 1/2012 | Ponce |
| 8,133,201 B1 | 3/2012 | Hurtado |
| 8,152,751 B2 | 4/2012 | Roger et al. |
| 8,162,884 B2 | 4/2012 | Van't Hooft |
| 8,211,056 B2 | 7/2012 | Cull |
| 8,414,530 B2 | 4/2013 | Mason |
| 8,439,873 B1 | 5/2013 | Donovan |
| 8,764,698 B2 | 7/2014 | Cull |
| 8,784,359 B2 | 7/2014 | Plahey et al. |
| 8,870,820 B2 | 10/2014 | Murphy et al. |
| 8,882,694 B2 | 11/2014 | Li et al. |
| 8,906,087 B2 | 12/2014 | House et al. |
| 8,961,458 B2 | 2/2015 | Pesach et al. |
| 8,992,453 B2 | 3/2015 | Vournakis et al. |
| 9,023,051 B2 | 5/2015 | Hanson et al. |
| 9,199,044 B2 | 12/2015 | Bangera et al. |
| 9,585,998 B2 | 3/2017 | Gage et al. |
| 9,694,145 B1 | 7/2017 | Onorato |
| 9,700,674 B2 | 7/2017 | Despa et al. |
| 9,757,515 B1 | 9/2017 | Patel |
| 1,017,301 A1 | 1/2019 | Fiedler et al. |
| 10,173,015 B2 | 1/2019 | Fiedler et al. |
| 10,420,874 B2 | 9/2019 | Gage et al. |
| 11,065,377 B2 | 7/2021 | Gage et al. |
| 2003/0100859 A1 | 5/2003 | Henderson et al. |
| 2004/0153031 A1 | 8/2004 | Van Kaauwen |
| 2004/0193106 A1 | 9/2004 | Miller |
| 2004/0022044 A1 | 11/2004 | Hogendijk et al. |
| 2005/0013850 A1 | 1/2005 | Caers et al. |
| 2005/0148935 A1 | 7/2005 | Dimitrova et al. |
| 2005/0267396 A1 | 12/2005 | Dame |
| 2006/0118236 A1 | 6/2006 | House et al. |
| 2007/0123811 A1 | 5/2007 | Squitieri |
| 2008/0146963 A1 | 6/2008 | Crocker et al. |
| 2008/0195043 A1 | 8/2008 | Schwach et al. |
| 2008/0221519 A1 | 9/2008 | Schwach et al. |
| 2009/0209921 A1 | 8/2009 | Claude et al. |
| 2010/0015590 A1 | 1/2010 | Kiss |
| 2011/0060264 A1 | 3/2011 | Porter et al. |
| 2011/0202003 A1 | 8/2011 | Cook |
| 2011/0275930 A1 | 11/2011 | Cox et al. |
| 2012/0245536 A1 | 9/2012 | Gerber et al. |
| 2012/0265138 A1 | 10/2012 | Harylka et al. |
| 2013/0072883 A1 | 3/2013 | Edoga et al. |
| 2013/0157924 A1 | 6/2013 | Dewhurst et al. |
| 2013/0237929 A1 | 9/2013 | Hong et al. |
| 2014/0018721 A1 | 1/2014 | Gage et al. |
| 2014/0039453 A1 | 2/2014 | Sonderegger |
| 2014/0128842 A1 | 5/2014 | Deberadine |
| 2014/0155819 A1 | 6/2014 | Amirouche et al. |
| 2014/0200515 A1 | 7/2014 | Patterson et al. |
| 2014/0257183 A1 | 9/2014 | Mica et al. |
| 2014/0324021 A1 | 10/2014 | Ulrich et al. |
| 2014/0336682 A1 | 11/2014 | Naoum |
| 2015/0223906 A1 | 8/2015 | O'Neill et al. |
| 2016/0136363 A1 | 5/2016 | McClellan |
| 2016/0310663 A1 | 10/2016 | Dantsker |
| 2016/0310679 A1 | 10/2016 | Hirth |
| 2016/0354112 A1 | 12/2016 | Kustra et al. |
| 2016/0375193 A1 | 12/2016 | Farzam et al. |
| 2017/0173252 A1 | 6/2017 | Gage et al. |
| 2017/0203053 A1 | 7/2017 | Burkett |
| 2017/0340840 A1 | 11/2017 | Sweis |
| 2018/0185059 A1 | 7/2018 | Rowe |
| 2018/0193031 A1 | 7/2018 | Du et al. |
| 2018/0280605 A1 | 10/2018 | Gage et al. |
| 2018/0289883 A1 | 10/2018 | Gage et al. |
| 2018/0289901 A1 | 10/2018 | Boggild-Damkvist et al. |
| 2020/0016320 A1 | 1/2020 | Gage et al. |
| 2020/0129749 A1 | 4/2020 | Gage et al. |
| 2021/0346585 A1 | 11/2021 | Gage et al. |

FOREIGN PATENT DOCUMENTS

| | | |
|---|---|---|
| CN | 2693253 Y | 4/2005 |
| CN | 2855430 Y | 1/2007 |
| CN | 2875458 Y | 3/2007 |
| CN | 201211361 Y | 3/2009 |
| CN | 201596195 U | 10/2010 |
| CN | 201668815 U | 12/2010 |
| CN | 201996908 U | 10/2011 |
| CN | 202223661 U | 5/2012 |
| CN | 102580192 A | 7/2012 |
| CN | 102580193 A | 7/2012 |
| CN | 102580194 A | 7/2012 |
| CN | 102580195 A | 7/2012 |
| CN | 102580196 A | 7/2012 |
| CN | 102600532 A | 7/2012 |
| CN | 102600533 A | 7/2012 |
| CN | 102600534 A | 7/2012 |
| CN | 102631734 A | 8/2012 |
| CN | 103495244 A | 1/2014 |
| CN | 203389172 U | 1/2014 |
| CN | 203885933 U | 10/2014 |
| CN | 204181970 U | 3/2015 |
| CN | 204446835 U | 7/2015 |
| CN | 204619059 U | 9/2015 |
| CN | 204635146 | 9/2015 |

(56) References Cited

FOREIGN PATENT DOCUMENTS

| | | |
|---|---|---|
| CN | 204655694 U | 9/2015 |
| CN | 204655695 U | 9/2015 |
| CN | 204655696 U | 9/2015 |
| CN | 204745226 U | 11/2015 |
| CN | 105268063 A | 1/2016 |
| CN | 205031669 U | 2/2016 |
| CN | 205360154 U | 7/2016 |
| CN | 205515823 U | 8/2016 |
| CN | 205698760 U | 11/2016 |
| CN | 206183758 U | 5/2017 |
| CN | 107865990 A | 4/2018 |
| CN | 108114350 A | 6/2018 |
| CN | 108283756 A | 7/2018 |
| CN | 108525077 A | 9/2018 |
| DE | 102004037207 A1 | 4/2005 |
| EP | 1426067 A1 | 6/2004 |
| EP | 2686033 B1 | 5/2015 |
| FR | 2980977 | 4/2013 |
| GB | 2202445 | 9/1988 |
| KR | 101732305 | 5/2017 |
| WO | 8000060 | 1/1980 |
| WO | 2005002661 A1 | 1/2005 |
| WO | 2011112755 A2 | 9/2011 |
| WO | 12006790 A1 | 1/2012 |
| WO | 2012125927 A2 | 9/2012 |
| WO | 13061352 A1 | 5/2013 |
| WO | 2016179457 A1 | 11/2016 |
| WO | 18191121 A1 | 10/2018 |
| WO | 2018183854 A1 | 10/2018 |
| WO | 2018183886 A1 | 10/2018 |
| WO | 2020/092441 A1 | 5/2020 |

OTHER PUBLICATIONS

Gage, Shawn; Office Action for Japanese patent application No. 2020-502524, filed Mar. 30, 2018, dated Apr. 18, 2022, 16 pgs.

Gage, Shawn M.; Non-Final Office Action for U.S. Appl. No. 15/941,790, filed Mar. 30, 2018; dated Jul. 20, 2020; 50 pages.

Gage, Shawn M.; International Preliminary Report and Patentability and Written Opinion for PCT Application No. PCT/US2019/058665, filed Oct. 29, 2019; dated May 14, 2021; 10 pages.

Gage, Shawn M.; International Search Report and Written Opinion for PCT Application No. PCT/US2019/058665 filed Oct. 29, 2019; dated Apr. 2, 2020; 16 pages.

Gage, Shawn M.; Notice of Allowance for U.S. Appl. No. 15/941,599, filed Mar. 30, 2018, dated Mar. 16, 2021, 22 pgs.

Gage, Shawn M; Invitation to Pay Additional Fees for serial No. PCT/US2018/025414, filed Mar. 30, 2018, dated Jun. 27, 2018, 18 pgs.

Gage, Shawn M.; Final Office Action for U.S. Appl. No. 16/175,698, filed Oct. 30, 2018, dated Jan. 22, 2021, 24 pgs.

Gage, Shawn M.; Non-Final Office Action for U.S. Appl. No. 15/941,599, filed Mar. 30, 2018, dated Jan. 8, 2019, 14 pages.

Gage, Shawn M.; Requirement for Restriction/Election for U.S. Appl. No. 15/941,599, filed Mar. 30, 2018, dated Oct. 16, 2018, 8 pages.

Gage, Shawn; Final Office Action for U.S. Appl. No. 15/941,599, filed Mar. 30, 2018, dated Sep. 20, 2019, 29 pages.

Gage, Shawn M.; Non-Final Office Action for U.S. Appl. No. 14/027,986, filed Sep. 16, 2013, dated Apr. 1, 2016, 13 pgs.

Gage, Shawn M.; Restriction Requirement for U.S. Appl. No. 14/027,986, filed Sep. 16, 2013, dated Jan. 13, 2016, 9 pgs.

Gage, Shawn M.; Issue Notification for U.S. Appl. No. 14/027,986, filed Sep. 16, 2013, dated Feb. 15, 2017, 1 pg.

Gage, Shawn M.; Notice of Allowance for U.S. Appl. No. 14/027,986, filed Sep. 16, 2013, dated Nov. 2, 2016, 7 pgs.

Gage, Shawn M.; Non-Final Office Action for U.S. Appl. No. 15/450,523, filed Mar. 6, 2017, dated Jan. 23, 2019, 9 pgs.

Gage, Shawn M.; Requirement for Restriction/Election for U.S. Appl. No. 15/450,523, filed Mar. 6, 2017, dated Jul. 12, 2018, 9 pgs.

Gage, Shawn, Notice of Allowance for U.S. Appl. No. 15/450,523, filed Mar. 6, 2017, dated May 17, 2019, 7 pages.

Gage, Shawn M; International Search Report and Written Opinion for serial No. PCT/US2018/025414, filed Mar. 30, 2018, dated Aug. 21, 2018, 20 pgs.

Gage, Shawn; International Preliminary Report on Patentability for PCT Application No. PCT/US2018/025414, filed Mar. 30, 2018; dated Oct. 10, 2019; 15 pages.

Gage, Shawn M; International Preliminary Report on Patentability for serial No. PCT/US2012/029449, filed Mar. 16, 2012, dated Sep. 26, 2013, 6 pgs.

Gage, Shawn M; International Search Report and Written Opinion for serial No. PCT/US2012/029449, filed Mar. 16, 2012, dated Oct. 29, 2012, 8 pgs.

Gage, Shawn M.; Office Action for Australian serial No. 2012229032, filed Mar. 16, 2012, dated Feb. 9, 2015, 3 pgs.

Gage, Shawn M.; Office Action for Canadian serial No. 2,829,766, filed Mar. 16, 2012, dated Jan. 10, 2018, 5 pgs.

Gage, Shawn M.; Extended European Search Report for serial No. 12757046.3, filed Mar. 16, 2012, dated Jan. 3, 2014, 7 pgs.

Gage, Shawn M.; Decision to Grant for European serial No. 12757046.3, filed Mar. 16, 2012, dated Apr. 10, 2015,2 pgs.

Gage, Shawn M.; Intention to Grant for European serial No. 12757046.3, filed Mar. 16, 2012, dated Nov. 19, 2014,8 pgs.

Gage, Shawn M.; International Search Report and Written Opinion for serial No. PCT/US2018/025456, filed Mar. 30, 2018, dated Jun. 25, 2018, 12 pgs.

Gage, Shawn; International Preliminary Report on Patentability for PCT Application No. PCT/US2018/025456, filed Mar. 30, 2018; dated Oct. 10, 2019; 10 pages.

Gage, et al., "New Developments in Hemodialysis Grafts," Endovascular Today, Jun. 2010, pp. 38-44.

Gage, Shawn M.; Corrected Notice of Allowance for U.S. Appl. No. 15/941,599, filed Mar. 30, 2018, dated Apr. 28, 2021, 6 pgs.

Gage, Shawn M.; Applicant-Initiated Interview Summary for U.S. Appl. No. 16/175,698, filed Oct. 30, 2018, dated Jun. 25, 2021, 3 pgs.

* cited by examiner

APPARATUS AND METHOD FOR CANNULATION OF VASCULAR ACCESS VESSEL

CROSS-REFERENCES

This application is a divisional application of U.S. patent application Ser. No. 16/175,698, filed Oct. 30, 2018, the contents of which is incorporated herein by reference in its entirety.

STATEMENT REGARDING FEDERALLY SPONSORED RESEARCH OR DEVELOPMENT

This invention was made with government support under contract number NIH R41DK108488 awarded by the National Institute of Heath. The government has certain rights in the invention.

BACKGROUND

An apparatus and method is described for needle access of a surgically created vascular access for use as a means to receive hemodialysis and other procedures requiring vascular access and, more particularly, an apparatus and method for vascular access of an arteriovenous fistula or arteriovenous graft that enables location of cannulation sites post-implant.

Hemodialysis is a life-sustaining treatment for patients with end stage renal disease. Hemodialysis is a process whereby large amounts of blood are removed from the body, filtered through a machine that removes wastes, and then returned into the body.

A vascular access site on the body where blood will be removed and returned during hemodialysis is prepared before starting hemodialysis. High-flow access to a patient's circulation is achieved in a surgical anastomosis creating an arteriovenous fistula ("AVF") in which a vein is connected directly to an artery. Alternatively, the connection between the artery and the vein may be formed using a prosthetic arteriovenous graft ("AVG") made from a synthetic material and implanted just under the skin. Placement sites for AVG's include, without limitation, the forearm, upper arm, neck, chest, and thigh, in either straight or looped configurations.

Once a vascular access vessel is surgically positioned, the AVF or AVG becomes a conduit that can be used repeatedly for vascular access during hemodialysis. Needles are used to cannulate through the skin, directly puncturing the walls of the vascular access vessel. In conventional hemodialysis, two cannulas are placed in the vascular access vessel, with one efferent needle puncture being made in the graft wall in the arterial side and another afferent needle puncture being made in the venous side. During dialysis, blood is withdrawn from the arterial side via the first needle, passed through a hemodialysis machine, and then returned to the patient through the second needle inserted in the venous.

A significant step in the hemodialysis procedure is "finding" the proper position within along the vascular access vessel to perform the needle sticks. Moreover, conventional dialysis protocols require a patient to undergo a dialysis procedure at least three times a week. As a result, the skin and underlying tissue are punctured numerous times per week to gain entry into the vascular access vessel. The technique of cannulating an AVF or AVG for hemodialysis requires considerable skill. A vascular access vessel often lies several centimeters below the surface of the skin and cannot be located by visual inspection. A medical technician is required to locate the AVF or AVG by palpation, which can prove to be extremely difficult. The punctures of the vascular access are prone to error and complication. Punctures done incorrectly may promote rupture of the access, bleeding, hematoma formation, pseudoaneurysm formation, severe pain or the development of organized thrombi within the lumen of the graft. The formation of such blood clots may result not only in multiple graft thromboses, but may eventually lead to graft failure. Missing the vascular access entirely or improperly positioning of the needle within the lumen of the AVF or AVG device are two contraindications, which adversely affect the time the graft remains patent. Locating the cannulation area simply by using conventional methods of palpating through the skin is sometimes unreliable.

Chronic repeated insertion of the needles eventuates in traumatic breakdown of the skin, and traumatic breakdown and stenosis of the graft site, particularly in the vicinity of its venous anastomosis. Traumatic breakdown and stenosis requires thrombectomies, AVG salvage, surgical revision procedures and new surgical constructions. Vascular access life may be prolonged with patch angioplasty at venous outflow stenoses or by adding a new segment of the AVG to bypass areas of venous stenosis. Vascular access life may also be prolonged by rotating and tracking puncture sites to allow maximum healing between punctures at a particular site.

For the forgoing reasons, there is a need for an apparatus and method for proper cannulation of a vascular access fistula or graft, including correct identification of an access region of the vascular access following implantation. The new apparatus should improve access to the implanted AVF or AVG by allowing a user of the vascular access vessel to facilitate accurate and reproducible entry into the implanted AVF or AVG of dialysis needles, cannulas, and the like, which are introduced into the vascular access via insertion through the skin. Ideally, the new apparatus and method should minimize trauma, pain and risk of infection while also maximizing the functional integrity and longevity of the fistula or graft used in hemodialysis.

SUMMARY

An apparatus is provided for rotatable selection of sites for cannulation with a needle along a subcutaneous vascular access vessel. The cannulation site selection apparatus comprises a template having an inner surface and an outer surface, and a plurality of visible markings on the outer surface of the template. The template is adapted to be disposed adjacent the subcutaneous vascular access vessel such that the markings align with the cannulation sites along the vascular access vessel for selecting a site for cannulation with a needle into the vascular access vessel.

The vascular access vessel may be an arteriovenous dialysis access graft subcutaneously implanted in a body of a patient or an arteriovenous fistula in a body of a patient.

In one aspect, the plurality of visible markings on the template comprises an amount of cannulation site selection markings such that a user can cannulate the vascular access vessel at a different cannulation site selection marking for four weeks of treatment. The plurality of visible markings may be on a first side and a second side of a longitudinal axis of the template.

In a further aspect, the template may comprise a key on the template, the key describing the schedule for rotation of the cannulation site selection markings. The key can include a reproduction of an image of a forearm and a wrist of a patient and, further, a reproduction of an image of a torso of a patient.

In one aspect, the template has at least one passage opening, the template defines holes along an edge of the template, the holes spaced at set distances from one another, and is adapted to be disposed adjacent the subcutaneous vascular access vessel such that the holes align with the cannulation sites along the vascular access vessel for selecting a site for cannulation with a needle into the vascular access vessel.

In yet another aspect, the template is translucent.

A sleeve may be provided, the sleeve defining a pocket for receiving the template, wherein the sleeve is configured to accommodate the body of the subject adjacent the subcutaneous vascular access vessel such that the markings align with the cannulation sites along the vascular access vessel for selecting a site for cannulation with a needle into the vascular access vessel. In this embodiment, the vascular access vessel is an arteriovenous dialysis access graft subcutaneously implanted in a body of a patient, or an arteriovenous fistula in a body of a patient.

A kit is also provided, the kit comprising at least one dialysis needle for accessing a subcutaneous vascular access vessel in a body of a patient, a dispenser, a template having an inner surface and an outer surface, and a plurality of visible markings on the outer surface of the template. The template is adapted to be disposed adjacent the subcutaneous vascular access vessel such that the markings align with cannulation sites along the vascular access vessel for selecting a site for cannulation with the needle into the vascular access vessel.

In another embodiment, an apparatus for rotatable selection of a cannulation sites along a vascular access vessel comprises a template having an inner surface and an outer surface, the template defining at least one opening extending from the outer surface to the inner surface, and a skin marking device. The template is adapted to be disposed adjacent the subcutaneous vascular access vessel such that the at least one opening aligns with a cannulation site along the vascular access vessel for selecting the site for cannulation with a needle into the vascular access vessel by marking through the opening with the skin marking device. A spacer may be provided, the spacer defining a hole to be aligned with the last cannulation site for marking the arm beyond the periphery of the spacer.

A method is also contemplated for rotatable selection of sites for cannulation with a needle along a subcutaneous vascular access vessel. The cannulation site selection method comprises the steps of providing a template having an inner surface and an outer surface, disposing a plurality of visible markings on the outer surface of the template, positioning the template adjacent the subcutaneous vascular access vessel such that the markings align with the cannulation sites along the vascular access vessel, and selecting a site for cannulation with a needle into the vascular access vessel.

In one aspect, the cannulation site selection method further comprises the step of cannulating the vascular access vessel at a site corresponding to a second cannulation site selection marking, wherein the second cannulation site selection marking is spaced from the first cannulation site selection marking. Moreover, the step of cannulating the vascular access vessel at a site corresponding to a third cannulation site selection marking follows, wherein the third cannulation site selection marking is spaced from the second cannulation site selection marking. The plurality of visible markings on the template comprises an amount of cannulation site selection markings such that a user can cannulate the vascular access vessel at a different cannulation site selection marking for four weeks of treatment.

The cannulation site selection method may further comprise the step of implanting an arteriovenous dialysis access graft in a body of a patient, or the step of surgically forming an arteriovenous fistula in a body of a patient.

In another aspect of the method, the cannulation site is cannulated to provide access to the vessel for single-needle hemodialysis.

BRIEF DESCRIPTION OF THE DRAWINGS

For a more complete understanding of the present apparatus and method, reference should now be had to the embodiments shown in the accompanying drawings and described below. In the drawings.

DESCRIPTION

As used herein, the term "vascular access" is used to mean access to a vessel comprising an intended surgical connection between an arterial and venous system through which blood flows from the artery to the vein. As noted above, this can be achieved by an anastomosis directly connecting a vein to an artery (AVF) or by utilizing a synthetic or autologous conduit for anastomosis to an artery at one end and a vein at the other end to connect the arterial and venous systems (AVG). Because there are many types of AVG's and associated components that are well known in the art and that may be utilized with the present apparatus and method, a more detailed description of these components is not required. It is understood that the present apparatus and method is not directed to only to AVF nor to any particular type of AVG. The vascular access apparatus and method described herein is for use in medical procedures requiring vascular access. Accordingly, the features described herein may be used with any conventional vascular access vessel including AVG's including, but not limited to, the AVG described by U.S. Pat. No. 9,585,998, the contents of which are hereby incorporated by reference herein in their entirety.

A similar application is shown and described in U.S. Pub. Application No. 2014/0336682, the contents of which are also incorporated by reference herein in their entirety. Accordingly, detailed explanations of the functioning of all of the components and use of vascular grafts are deemed unnecessary for understanding of the present description by one of ordinary skill in the art.

Certain terminology is used herein for convenience only and is not to be taken as a limiting. For example, words such as "upper," "lower," "left," "right," "horizontal," "vertical," "upward," "downward," "top" and "bottom" merely describe the configurations shown in the FIGs. Indeed, the components may be oriented in any direction and the terminology, therefore, should be understood as encompassing such variations unless specified otherwise. The words "interior" and "exterior" refer to directions toward and away from, respectively, the geometric center of the core and designated parts thereof. The terminology includes the words specifically mentioned above, derivatives thereof and words of similar import.

Figure 1:
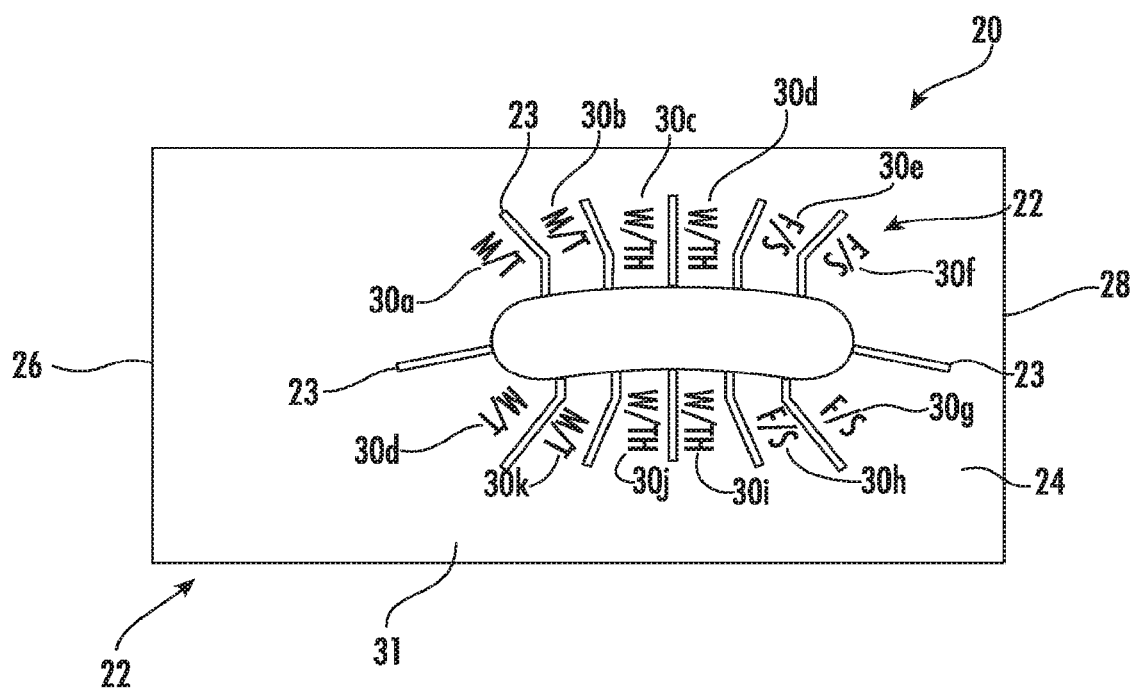
FIG. 1 is a top plan view of an embodiment of an apparatus for cannulation of a vascular access vessel.

Referring now to the drawings, wherein like reference numerals designate corresponding or similar elements throughout the several views, an apparatus for use in a method for cannulating a vascular access vessel connecting an artery to a vein is shown in FIG. 1 and generally designated at 20. The cannulation template 20 has markings 22 used to locate and implement cannulation at a site as well as for presenting a rotation plan for successive cannulations. The cannulation template 20 provides a device for rotatable selection of cannulation sites along a vascular access vessel for hemodialysis. As a result, the vascular access vessel is allowed increased healing time before re-cannulation occurs at a particular site. Properly spacing and rotating cannulation sites using the cannulation template 20 can extend the life of an arteriovenous fistula or arteriovenous graft and reduce the likelihood of failure of the vascular access. The cannulation template 20 as described herein can also be used to assist users with properly inserting a needle into a site to carry out hemodialysis treatments.

FIG. 1 shows a first outer side 24 of an embodiment of the cannulation template 20 to be used for a patient with, for example, an arteriovenous graft. The cannulation template has a left end 26 and a right end 28. The outer side 24 surface has markings 22 for the user to plan and select cannulation sites. More particularly, the cannulation template 20 has a first marking 30a located, for example, at one end of the cannulation template 20, and additional markings extending the length 31 thereof. In use, the first marking 30a is positioned adjacent the anastomosis made surgically between adjacent blood vessels, or other channels of the body, and indicates a first site for cannulation.

In one embodiment, the cannulation template 20 is made of a flexible material. The cannulation template 20 may, for example, be made of a flexible plastic, although paper, metal foil or a substantially equivalent material is suitable. The material from which the cannulation template 20 is formed is sufficiently flexible such that the apparatus can be bent around a patient's body part without breaking. This configuration of the cannulation template 20 allows a user to orient the cannulation template 20 appropriately along a patient's arteriovenous fistula or graft. As a result, the cannulation template 20 may be easily contoured along a vascular access vessel allowing selection of a cannulation site regardless of the vessel geometry.

Referring to FIG. 1, the cannulation template 20 has an array of markings 22 along the length 31. The markings 22 include boundary lines 23 providing an exemplary hemodialysis access configuration comprising an array of twelve cannulation sites, indicated in FIG. 1 by reference numerals 30a through 30l. Each of reference numerals 30a-30l indicates a site where along the vascular access vessel cannulation should occur for hemodialysis treatment. The array of cannulation sites 30a-30l is used in a rotatable selection of a series of hemodialysis cannulation sites along an AVF or AVG for hemodialysis access of a patient. The user determines the number of available cannulation sites along the vascular access vessel based on the number of cannulation site markings corresponding to viable locations for cannulation along the vessel. Based on the number of available cannulation sites, the user has a defined number of treatments that can be completed before repeating a cannulation site. As shown in FIG. 1, the array includes twelve indicators 30a-30l for cannulation sites at which a hemodialysis needle may be cannulated. Each cannulation site corresponds with a cannulation site reference numeral 30a-30l. Each correspondingly labeled access site is an indicator where an arterial access needle and a venous access hemodialysis needle may be independently or simultaneously cannulated. In this embodiment, the cannulation sites associated with reference numerals 30a, 30e and 30j will be cannulated during week 1, the cannulation sites associated with reference numerals 30d, 30g and 30k will be cannulated during week 2, the cannulation sites associated with reference numerals 30b, 30f and 30i will be cannulated during week 3, and the cannulation sites associated with reference numerals 30c, 30h and 30l will be cannulated during week 4. The indicated sites 30a-30l represent arterio-venous cannulation sites that are properly spaced and successively employed in an exemplary twelve successive hemodialysis sessions that comprise an exemplary hemodialysis cycle. With twelve available cannulation sites, given that the patient requires three hemodialysis treatments per week, a four week rotation plan for cannulation sites is provided. Each treatment may use a new site until treatment at the site 30l is completed. Then, at the next treatment, the user would return to re-cannulate site 30a. The user will then cannulate at each of the subsequent chosen cannulation sites in the same rotation. By sequentially using the paired arterial and venous hemodialysis needles along the pathway of the vascular access vessel, the maximum number of available cannulation sites to be used in subsequent treatments and cannulation trauma to the vessel is evenly distributed over time and repeated cannulation of the same sites is avoided. The longevity of the vascular access vessel is accordingly extended.

The markings 22 on the cannulation template 20 may also be of different colors so as to make the markings 22 easier to read or distinguish from one another. For example, the cannulation site reference numerals 30a-30l for each week may be in contrasting colors, such as red, blue, green and gold for weeks 1-4, respectively. Instead of visual means the markings 22 for the cannulation zones may be delineated by physical means, raised or recessed material that physically separates the individual zones.

Figure 3:
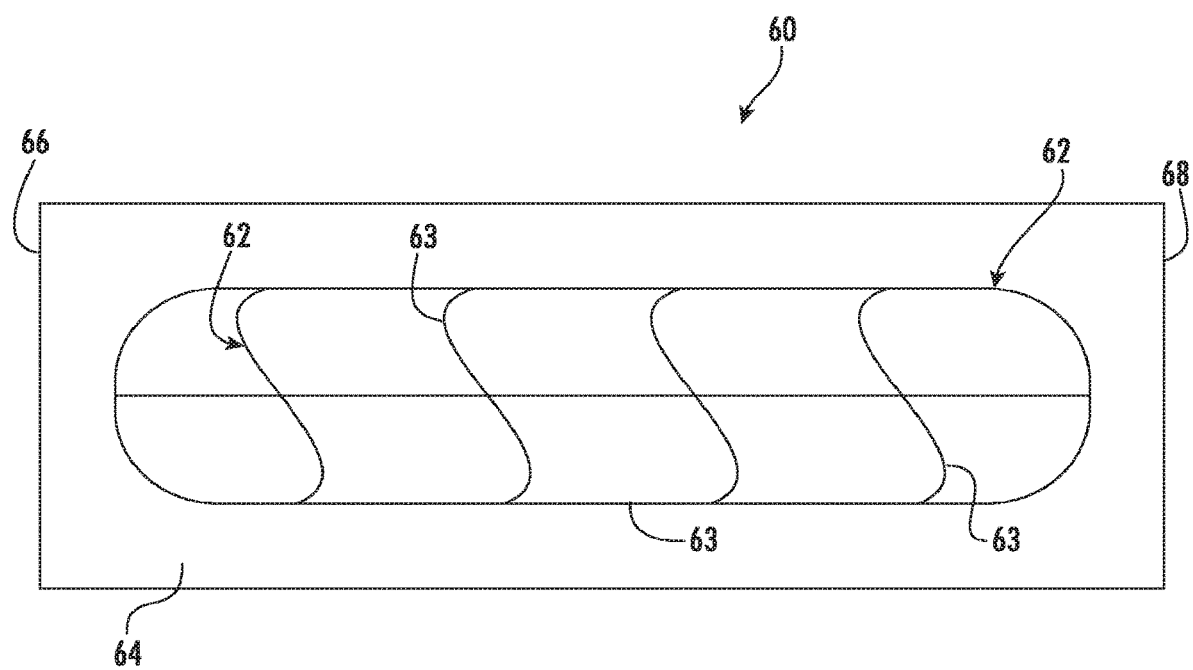
FIG. 3 is a top plan view of a third embodiment of an apparatus for cannulation of a vascular access vessel.

Similarly, the cannulation site reference numerals on the cannulation template may have differing shapes, for example, arrows for arterial access and lines for venous access. A cannulation template 60 is shown in FIG. 3, including an outer side 64 and having a left end 66 and a right end 68. The cannulation template 60 has markings 62 which, in this embodiment, includes physical boundary lines 63 spanning the opening in the template 60 and defining zones for the user to plan and select cannulation sites. The cannulation zones do not need to be set in a grid fashion, thus the shapes can be abstract and non-typical to maximize cannulation area or increase separation between needle sticks. The shape could be chosen to accommodate any vascular access vessel. The shape of the cannulation template 60 could include, but is not limited to, any shape intended to accomplish the goal of rotating needle sites.

The rectangular cannulation template 20 shown in FIG. 1 is about 2 inches long and about one-half inch wide. Adjacent cannulation sites are separated by about 0.5 centimeters to about 1 centimeter. However, these distances may differ based on a patient's condition. While the cannulation template 20 of the embodiment shown is rectangular in shape, other embodiments of the cannulation template 20 may other shapes and dimensions. For example, as shown in FIG. 1, a cannulation template may be have an ovular opening having a curved edge such that the apparatus could be placed along a curved vascular access vessel for determining available cannulation sites or measuring from one site to the next.

The markings 22 on the cannulation template 20 are substantially permanent so as not to be smudged or wiped away upon sterilization between uses. Sterilization may be performed by submerging the cannulation template 20 in a 1% bleach solution for twenty minutes. The markings 22 may be designed to withstand degradation during other sterilization procedures, which may include sterilization by ultraviolet light, a higher or lower concentration of bleach for a longer or shorter soaking time, or hydrogen peroxide. As a result, the cannulation template 20 is reusable and easy to clean. The markings 22 on the cannulation template 20 may be obtained by reproductive means, such as, for example, conventional photography, digital photography, manual drawing, digital imaging or substantially equivalent means. The hemodialysis access configuration represented by the markings 22 may be transferred to the cannulation template 20 by transfer means such as, for example, printing, lithography, photocopying, or substantially equivalent means. It is understood that other information may be printed on either surface of the cannulation template 20. For example, this arrangement allows for usage instructions to be printed on at least one side. Alternatively, the flexible member may be translucent.

The cannulation template 20 may be used with an arteriovenous fistula or arteriovenous graft. As described above, an arteriovenous graft hemodialysis access configuration surgically substitutes a conduit between an artery and a vein for a surgically created fistula. The description of the method that follows is in connection with the use of the AVG for hemodialysis. It is understood that the present vascular access configuration is equally applicable to a patient with the AVF for hemodialysis.

In use, a user places the cannulation template 20 on a patient's arm at the arteriovenous anastomosis, or another bodily area where vascular access is to be obtained. To determine a first cannulation site, the user orients the cannulation template 20 along the AVG used to create the vascular access. In orienting the cannulation template 20 along the vascular access vessel, the user places the left end 26 bearing the first markings 22 adjacent to the anastomosis. The flexibility of the material of the cannulation template 20 allows the user to contour the cannulation template 20 along the AVG. As the cannulation template 20 is contoured along the vessel, the first reference numeral 30a showing a label "M/T" indicates a first cannulation site in the array, creating a visual "stick zone" along the vessel indicating to the user that a pair of cannulation needles should be inserted in that area.

The user inserts a first cannulation needle at the site 30a for providing arterial vascular access to the patient. During hemodialysis treatment, the patient's blood will flow from the AVG, through the needle, and into tubing. The blood will pass through the tubing to an extracorporeal blood circuit and is returned through a venous needle inserted into the vascular vessel at the site 30a. When treatment is completed, the needles are removed, and the cannulated site 30a may begin to heal. Because of the design of the cannulation template 20, the first site 30a will typically not be re-cannulated until all other possible cannulation sites along the cannulation template 20 have been used. In this embodiment, site 30a will have four weeks to heal before re-cannulation.

When the patient requires a subsequent hemodialysis treatment, the user again begins by placing the first end of the cannulation template 20 at the anastomosis of the patient and orienting the cannulation template 20 along the AVG. The user will then select a different selection reference numeral 30j showing label "W/TH". It is understood that the user may assess the viability of the available cannulation sites. For example, if the cannulation site associated with reference numeral 30j along the AVG as identified by cannulation site selection marking is not viable based on the condition of the AVG, the user would then select the next subsequent site for cannulation.

The user cannulates the selected site 30j with a first needle to provide arterial vascular access to the AVG for hemodialysis treatment and a second needle to provide venous vascular access to the AVG. Blood is removed from the patient through the first needle and returned through the second needle. When treatment is completed, the needles are removed and the cannulated site 30j may begin to heal. The second suite 30j will typically not be re-cannulated until all other possible cannulation sites have been used. In this embodiment, the site 30j will have four weeks to heal before re-cannulation.

While the cannulation template 20 of the embodiments shown and discussed above are discussed mainly for use in cannulating a patient for hemodialysis treatments, the cannulation template 20 may be used in cannulating patients for hemofiltration, hemodiafiltration, ultrafiltration, or other medical treatments where cannulation or insertion of an instrument into the body at a particular position or angle is necessary.

The cannulation template 20 and method as described herein identifies successive hemodialysis needle cannulation sites along a marked pathway of a corresponding vascular access vessel. The cannulation template assists the user, whether an in-center dialysis technician or a self-cannulator, to use best practice in cannulating a vascular access vessel for hemodialysis to ensure proper needle site rotation to maximize tissue healing, reduce graft degradation, and provide a clear protocol for where and when to cannulate a vascular access vessel. Cannulation trauma to the vessel is evenly distributed over time and space, and repeated cannulation of the same sites is minimized. As a result, the longevity of the vascular access vessel is extended.

Figure 2:
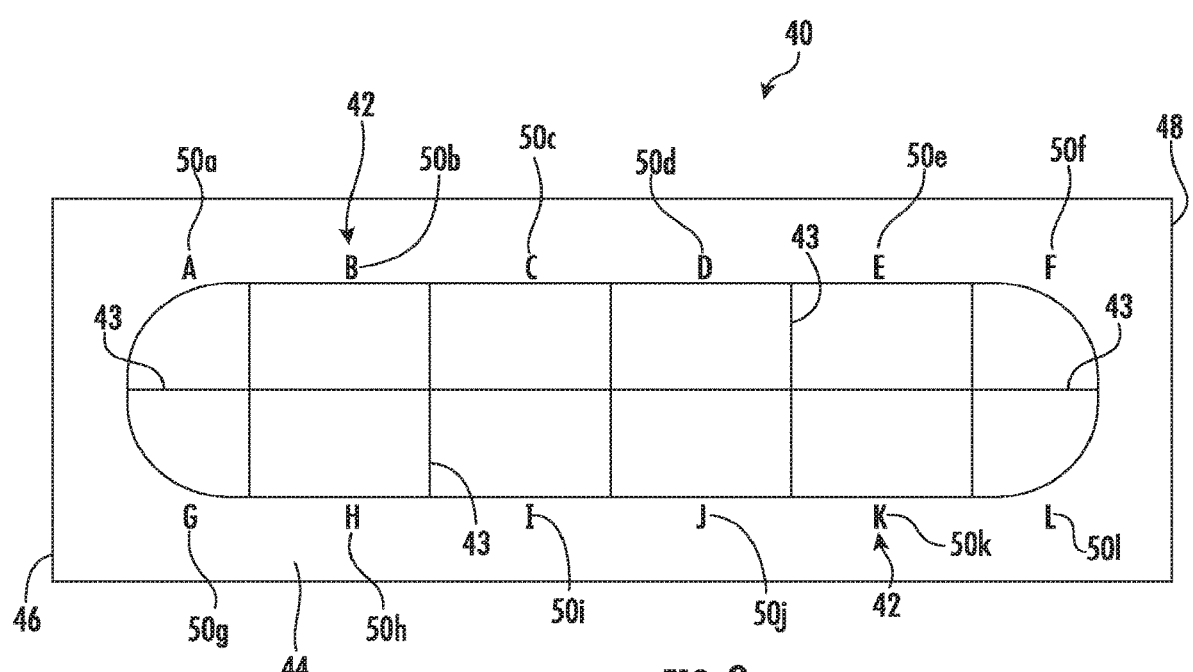
FIG. 2 is a top plan view of another embodiment of an apparatus for cannulation of a vascular access vessel.

FIG. 2 shows a second embodiment of a cannulation template generally designated at 40. The cannulation template 40 has an oval opening and includes markings 42 on an outer side 44 surface having a left end 46 and a right end 48. The cannulation template comprises boundary lines 43 spanning the opening and separating the template 40 into twelve cannulation zones 50a-50l. In use, the first marking 50a is positioned adjacent the anastomosis made surgically between adjacent blood vessels, or other channels of the body, and indicates a first site for cannulation. The array of markings 42 along the cannulation template 40 provides an exemplary hemodialysis access configuration comprising an array of twelve cannulation sites, indicated in FIG. 2 by labels A through L at reference numerals 50*a* through 50*l*. Each label 50*a*-50*l* indicates a site where cannulation should occur along the vascular access vessel for hemodialysis treatment. The array of cannulation sites is used in a rotatable selection of a series of hemodialysis cannulation sites along an AVF or AVG for hemodialysis access of a patient. Cannulation protocols can be developed based on the separate zones, which would facilitate the creation of a prospective cannulation 'schedule' to ensure the appropriate cannulation separation between needle sticks. The cannulation template 40 shown in FIG. 2 may be used to design a needle rotation schedule for one or two needles. In single needle dialysis, one needle is inserted into a vascular access vessel. The dialysis machine cycles between removing blood from the patient and delivering blood to the patient through the single needle. If the cannulation template 40 is used for one needle, for example, zones "A" 50*a*, "I" 50*i*, and "E" 50*e* can be used sequentially over the course of one week to ensure that each needle stick is spaced far enough apart to allow adequate tissue healing between sticks.

Figure 4:
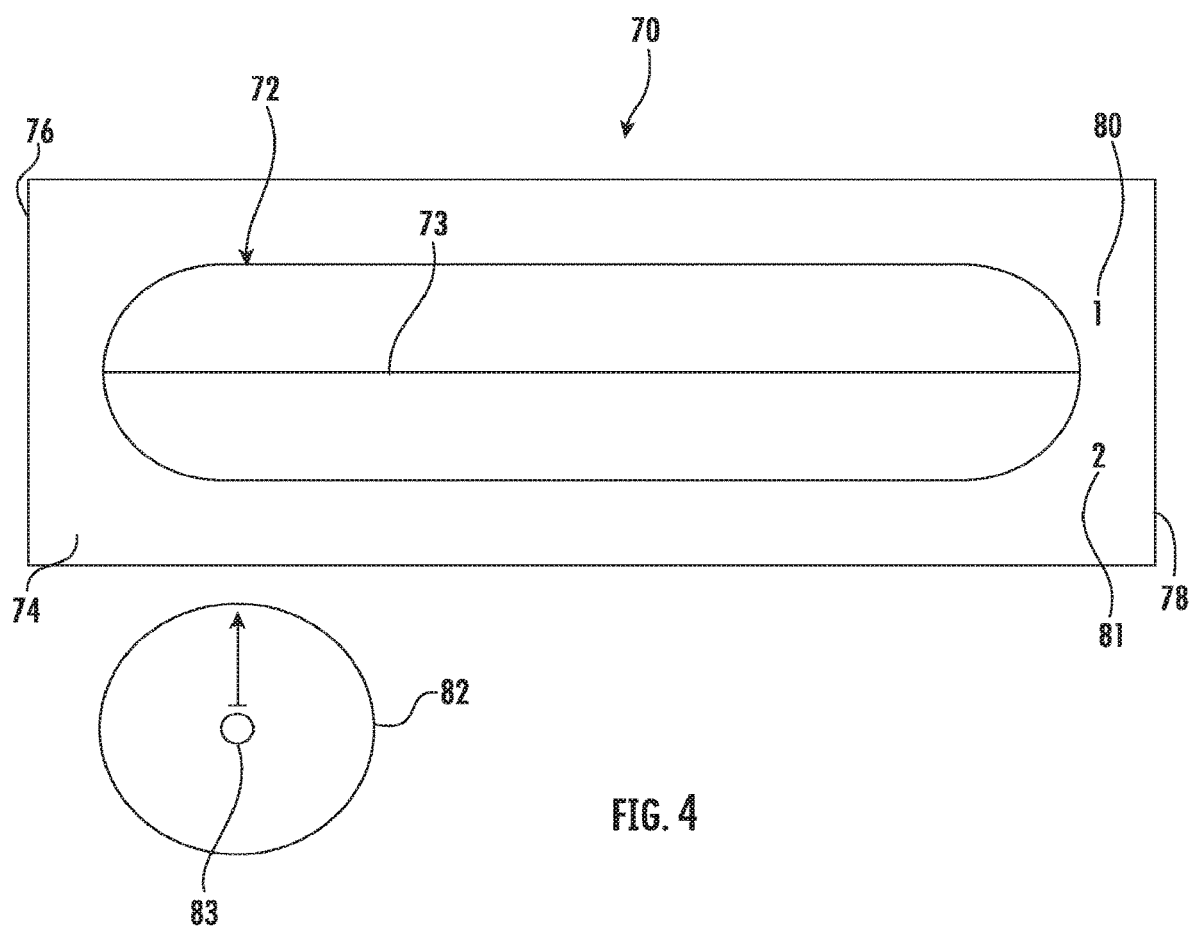
FIG. 4 is a top plan view of a fourth embodiment of an apparatus for cannulation of a vascular access vessel.

The cannulation template shown in FIG. 4, generally designated at 70, has an outer side 74 and a left end 76 and a right end 78. The cannulation template 70 has markings 72 including a boundary 73 spanning the opening and showing two areas of the template 70 that should be cannulated as indicated at reference numerals 80, 81. In this embodiment, the user employs a circular spacer 82 defining a central hole 83 and creates a marking on a patient's skin through the cannulation template where they intend to cannulate the patient's vascular access. The user thus has some freedom on where to cannulate next, given that the spacer always ensures adequate separation from a previous cannulation. In use, the hole 83 in the spacer 82 is aligned with the last cannulation site. The user can then cannulate anywhere outside of the spacer area. This distance is approximately 0.5 cm to about 1.0 cm to ensure appropriate separation and tissue healing between previous cannulation sites. The cannulation template 70 is then removed, and cleaned for dialysis initiation. Thus, the cannulation template 70 is not present when the dialysis session occurs and the needles are inserted into the patient's vascular access.

Figure 5:
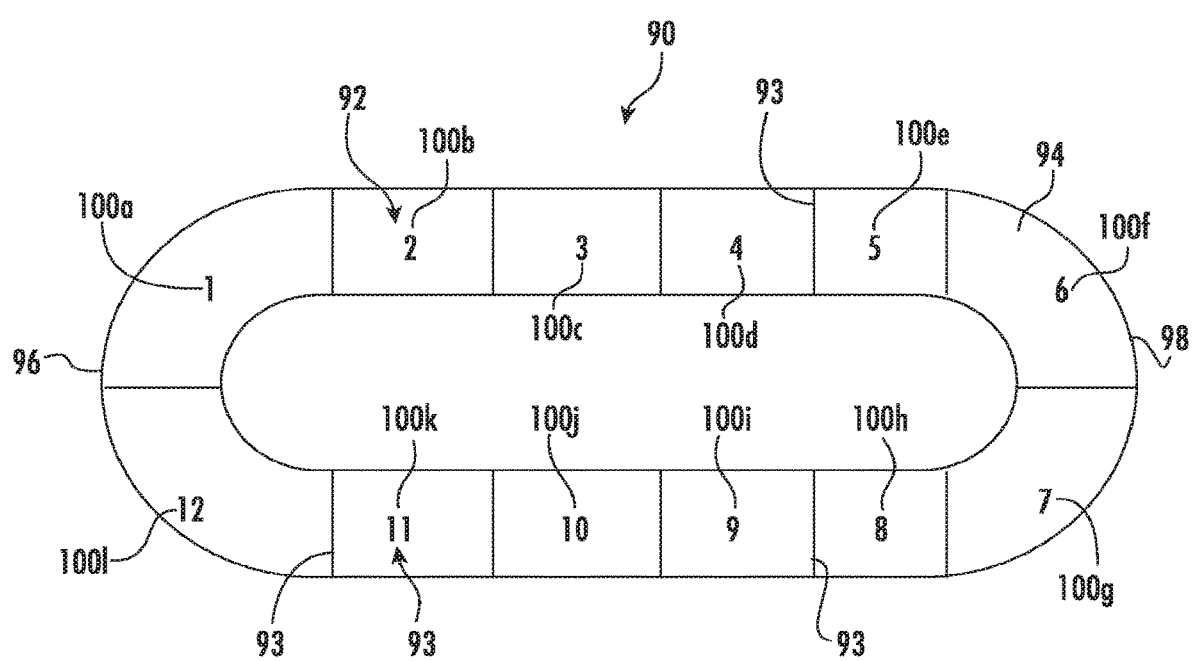
FIG. 5 is a top plan view of a fifth embodiment of an apparatus for cannulation of a vascular access vessel.

FIG. 5 shows a cannulation template generally designated at 90 wherein the cannulation area is unmarked. The cannulation template 90 has an outer side 94 and a left end 96 and a right end 98. Markings 92 and twelve labels 100*a*-100*l* separated by boundary lines 93 surround the cannulation area.

Figure 6:
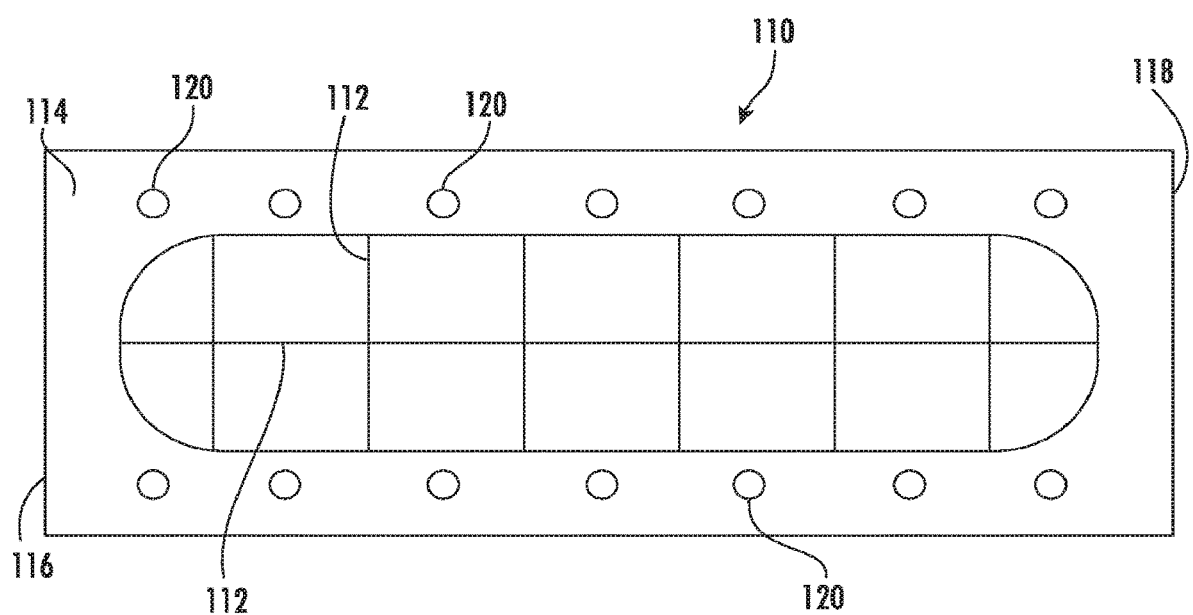
FIG. 6 is a top plan view of a sixth embodiment of an apparatus for cannulation of a vascular access vessel.

Another embodiment of a cannulation template not including markings is shown in FIG. 6 and generally designated at 110. The cannulation template 110 has an outer side 114 and a left end 116 and a right end 118. The cannulation template 110 has markings 112 spanning the opening. In this embodiment, tracking a hemodialysis configuration occurs on the cannulation template 110 itself. The cannulation template 110 comprises physical features to aid the user in selecting cannulation sites in lieu of, or in addition to, cannulation site markings. The cannulation template 110 has holes 120 along opposed longer edges which aid the user in visualizing cannulation sites as the holes may help to frame the cannulation sites. The holes 120 allow a physical item to be clipped, or a marker used to mark, or any other visual or physical component can be used to indicate a progression of previous cannulation sites. If a previous cannulation site is completely healed, other information is necessary to determine the previous cannulation site. In addition, holes in the body of the cannulation template 110 could allow cannulation through the flexible member. For example, the user could lay the cannulation template 110 against the vessel, determine cannulation sites, and cannulate through the hole 120 at that designated cannulation site.

Figure 7:
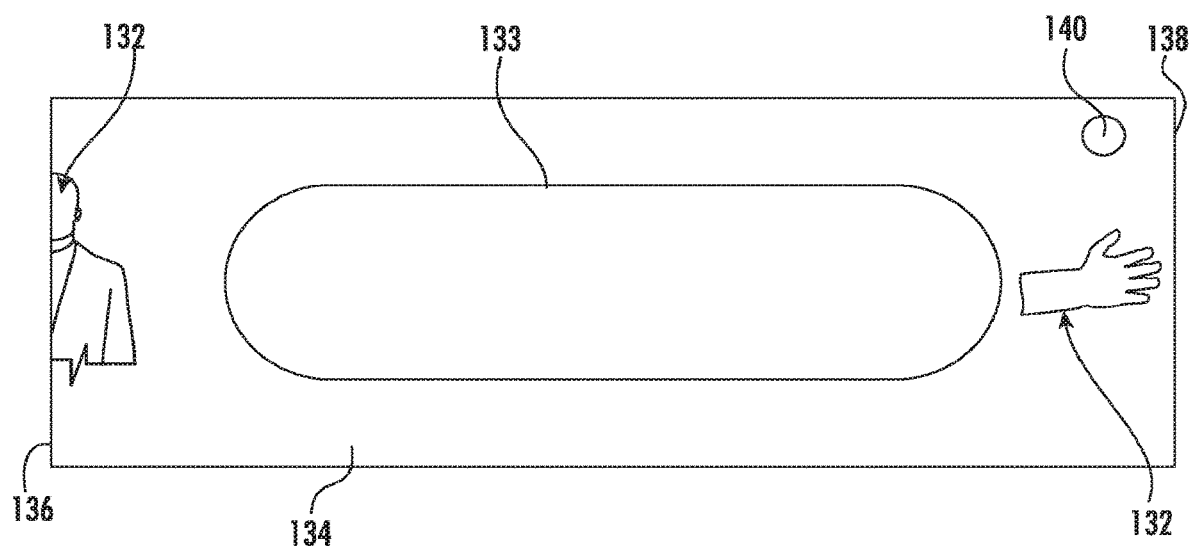
FIG. 7 is a top plan view of a seventh embodiment of an apparatus for cannulation of a vascular access vessel.

FIG. 7 shows a cannulation template 130 defining an oval opening 133. A key 132 on the template 130 indicates location and orientation of the cannulation template 130. In this embodiment, the cannulation template 130 is used on a forearm 132 for vascular access, which is shown on the template 130. The cannulation template 130 also includes a partial picture of a body of a person to indicate appropriate orientation, wherein one end 138 of the cannulation template 130 is oriented towards a user's hand and the other end 136 is oriented towards the user's body. Other visual cues may be used, such as using a permanent or temporary marking on a user's body or clothing to align with a feature on the cannulation template 130 such as a hole 140. The background of the cannulation template 130 on the surface 134 of the cannulation template 130 could also be printed to match with the location of a user's skin on which it is located (e.g. elbow crease, forearm veins, etc.).

Figure 8:
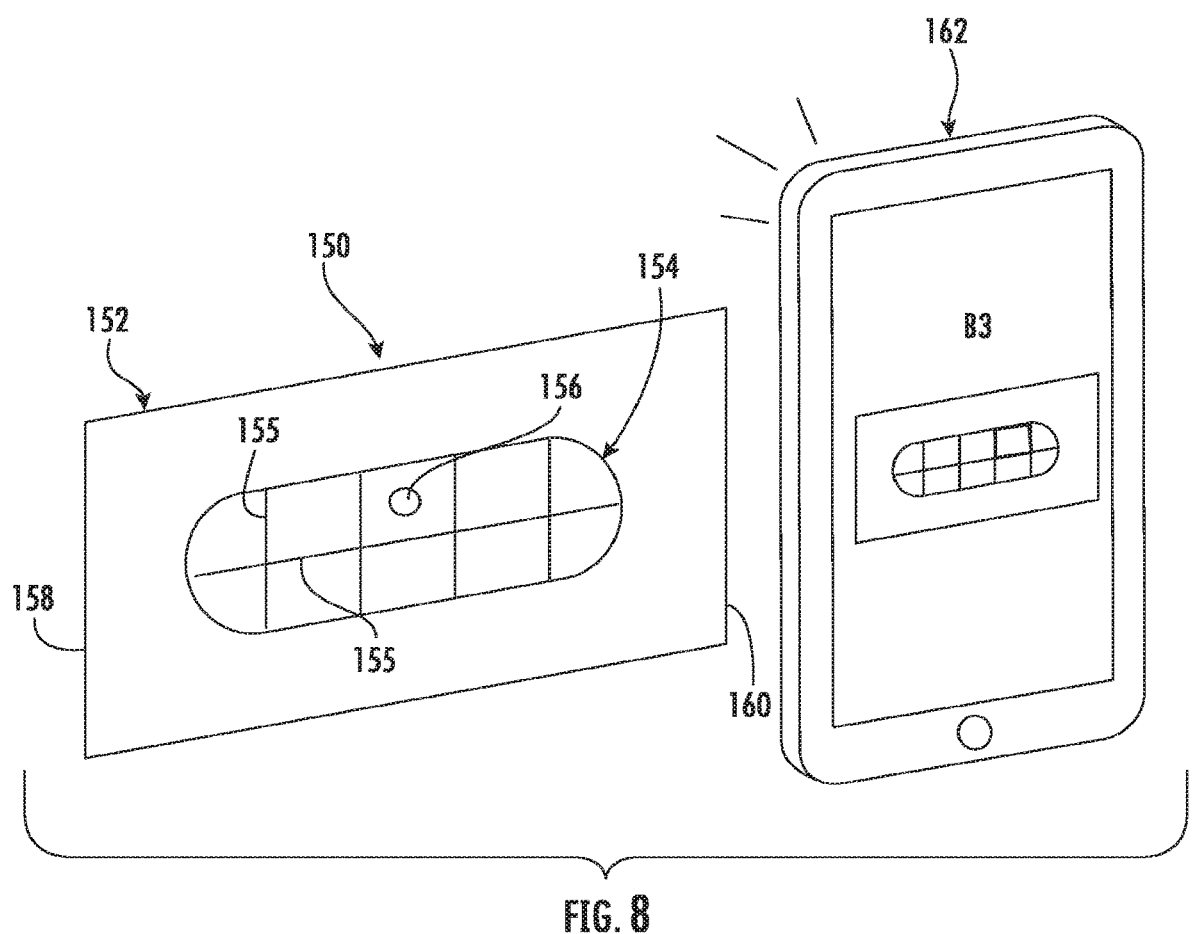
FIG. 8 is a perspective view of an eighth embodiment of an apparatus for cannulation of a vascular access vessel including a mobile telephone.

An embodiment of a cannulation template, generally designated at 150 in FIG. 8, can also be integrated with a software application for cannulation in a hemodialysis configuration. For example, a user could take a picture of a patient's arm, dialysis session, cannulation template 150, or other related item. The cannulation template 150 is similar to the embodiment shown in FIG. 2, having an oval opening 154 and includes markings 155 on an outer side 152 surface having a left end 158 and a right end 160. The markings 155 comprise boundary lines spanning the opening 154 and separating the template 150 into eight cannulation zones. The picture could be uploaded to a mobile device 162 or server to provide a procedural history of cannulation to allow an assessment of factors such as: A) where the graft has been cannulated most frequently, B) identification of cannulation sites around the time that adverse events are identified, C) evaluation of whether density of graft punctures may lead to adverse events such as pseudoaneurysms, D) total history of cannulation and location, E) a way to transmit data to care providers, etc. The platform could incorporate machine learning and/or artificial intelligence to aid in the tracking and diagnosing of medical events. A picture taken prior to a dialysis session and uploaded provides a recommendation to the user for where to cannulate based on a combination of, for example, previous cannulation sites, previous adverse events, rates of tissue healing, graft integrity, and the like.

Figure 9:
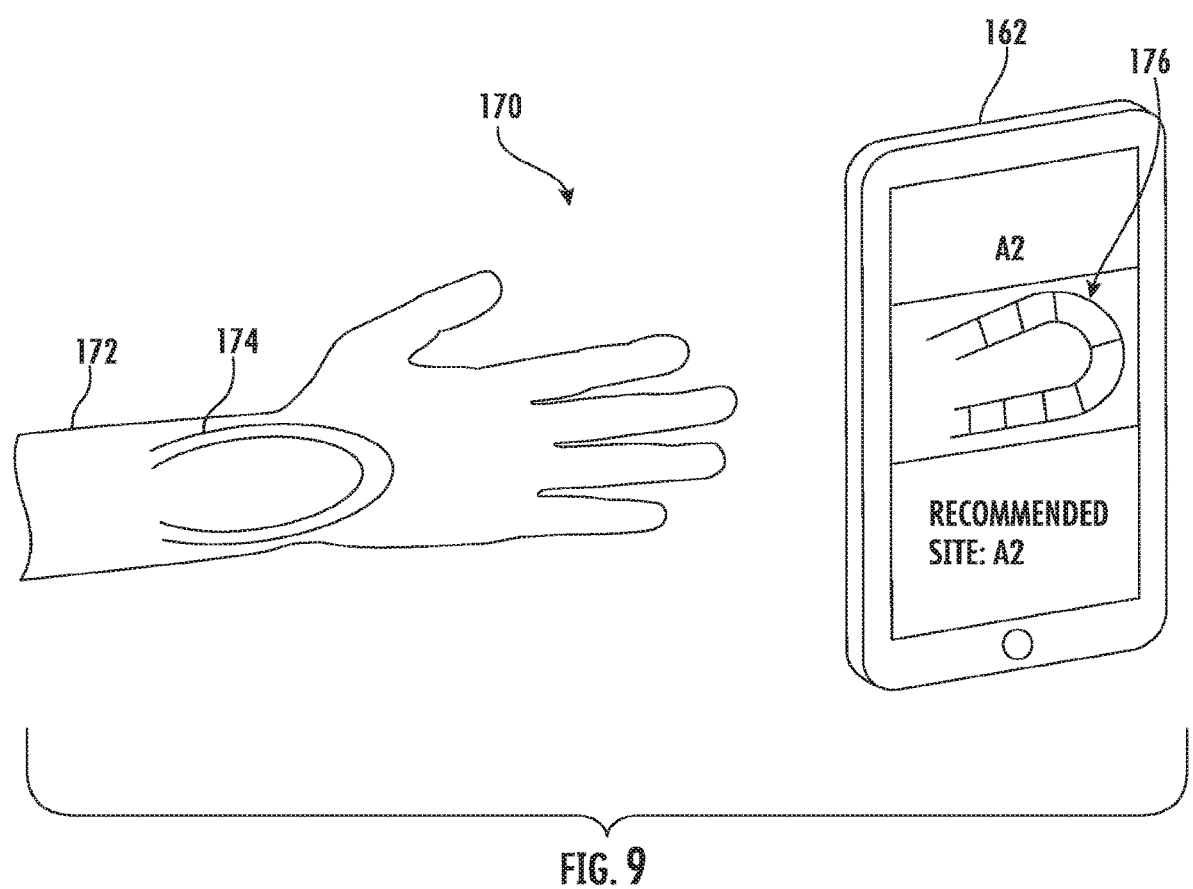
FIG. 9 is a perspective view of another embodiment of an apparatus for cannulation of a vascular access vessel including a mobile telephone.

FIG. 9 shows an embodiment of a cannulation method 170 similar to FIG. 8 wherein a physical cannulation template is not necessary. A picture 176 of the vascular access vessel 174 in forearm 172 is uploaded to a mobile device 162 including software provides a digital cannulation template interface and recommends cannulation site for vascular access.

Figure 10:
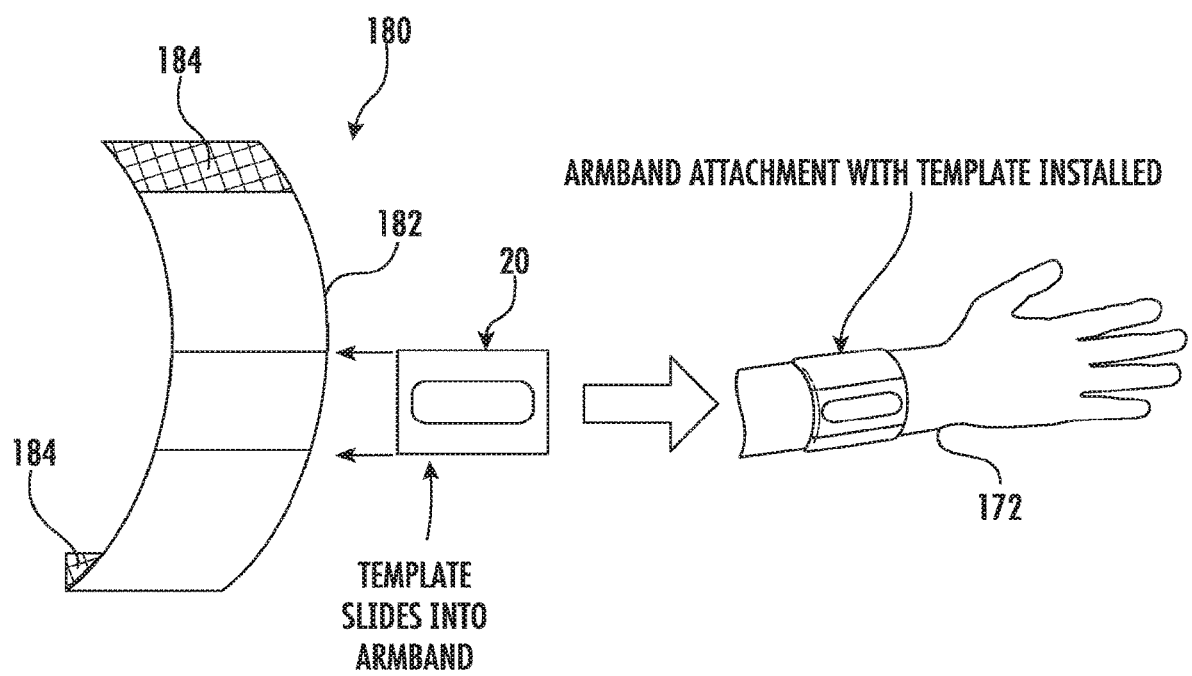
FIG. 10 is a schematic perspective view of an embodiment of a wristband for use with an apparatus for cannulation of a vascular access vessel.

FIG. 10 shows an embodiment of a cannulation method 180 comprising an armband 182 or any other flexible, semi-rigid or rigid item. The armband is adapted to receive the cannulation template 20 for attachment to the forearm 172 of a patient. The armband 182 may be secured around the forearm 172 using attachment means 184, such as Velcro, at the free ends of the armband 182.

Figure 11:
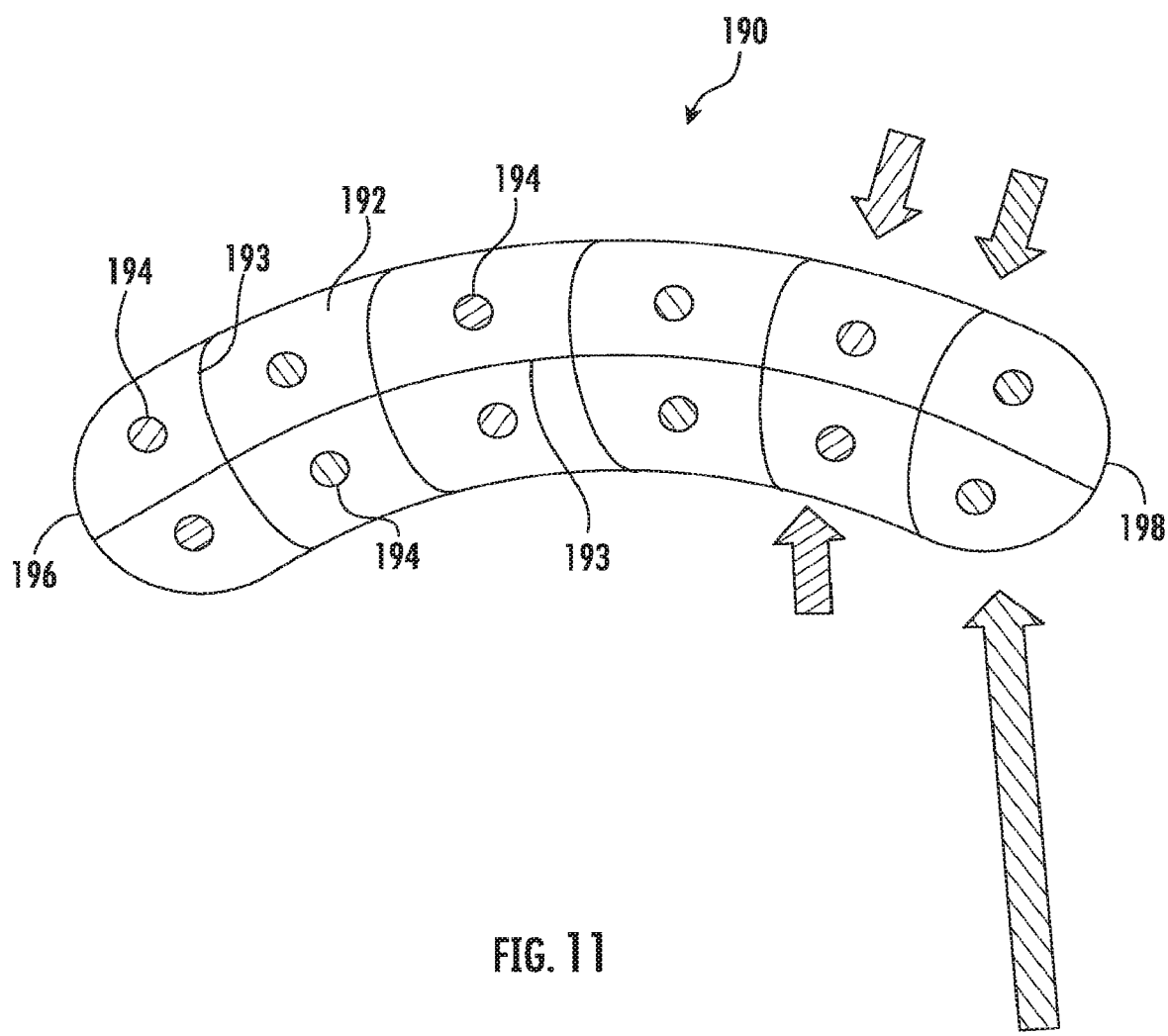
FIG. 11 is a top plan view of a ninth embodiment of an apparatus for cannulation of a vascular access vessel.

In FIG. 11, a slightly arcuate embodiment of a cannulation template is generally designated at 190. The cannulation template 190 has an openings 194 in an outer side 192 surface having a left end 196 and a right end 198. The cannulation template 190 comprises boundary lines 193 between the openings 194 for separating the template 190 into twelve cannulation zones. It is contemplated that each of the 193 boundary lines comprise different colors to indicate cannulation sites and protocols to ensure appropriate needle rotation.

Although cannulation templates and method have been shown and described in considerable detail with respect to only a few exemplary embodiments thereof, it should be understood by those skilled in the art that we do not intend to limit the apparatus and method to the embodiments since various modifications, omissions and additions may be made to the disclosed embodiments without materially departing from the novel teachings and advantages, particularly in light of the foregoing teachings. For example, the present cannulation template 20 and method is suitable for use in a number of vascular access devices and applications. While the cannulation template 20 shown and described are discussed in the context of cannulating a patient's arm, the cannulation template 20 may be used with other vascular access positions on a patient. These other positions may include, the leg, the neck, the chest, or the groin. Moreover, while the cannulation templates of the embodiments shown and discussed above are described mainly in the context of a two-needle vascular access procedure, the cannulation templates can also be used for single needle dialysis. Accordingly, we intend to sticker all such modifications, omission, additions and equivalents as may be included within the spirit and scope of the cannulation template 20 and method as defined by the following claims. In the claims, means-plus-function clauses are intended to sticker the structures described herein as performing the recited function and not only structural equivalents but also equivalent structures. Thus, although a nail and a screw may not be structural equivalents in that a nail employs a cylindrical surface to secure wooden parts together, whereas a screw employs a helical surface, in the environment of fastening wooden parts, a nail and a screw may be equivalent structures.

We claim:

1. A method for rotatable selection of sites for cannulation through skin of a patient of a subcutaneous vascular access vessel, the cannulation site selection method comprising steps of:
   providing a template having an inner surface and an outer surface, the template defining an opening for a plurality of zones, each of the plurality of zones configured for receiving a plurality of simultaneous cannulations accessing the vascular access vessel;
   marking the outer surface of the template, the marking defining each of the plurality of zones for use as cannulation sites along the vascular access vessel;
   positioning the template on the skin of the patient adjacent the subcutaneous vascular access vessel such that the opening aligns with the vascular access vessel; and
   using the marking for selecting a first zone for a cannulation site into the vascular access vessel such that the cannulation site in the first zone is spaced from and not adjacent to a second zone used for cannulation immediately previously to the first zone.

2. The cannulation site selection method as recited in claim 1, further comprising a step of cannulating the vascular access vessel through the skin of the patient at the cannulation site in the first zone.

3. The cannulation site selection method as recited in claim 1, further comprising a step of using the marking for selecting a corresponding third zone for a cannulation site into the vascular access vessel such that the third zone is spaced from and not adjacent to the first zone used for cannulation immediately previously to the third zone; and
   cannulating the vascular access vessel through the skin of the patient at the cannulation site in the third zone.

4. The cannulation site selection method as recited in claim 3, further comprising a step of using the marking for selecting a corresponding fourth zone for a cannulation site into the vascular access vessel such that the fourth zone is spaced from and not adjacent to the third zone used for cannulation immediately previously to the fourth zone; and
   cannulating the vascular access vessel through the skin of the patient at the cannulation site in the fourth zone.

5. The cannulation site selection method as recited claim 1, wherein the step of marking the template for defining each of the plurality of zones for use as cannulation sites along the vascular access vessel comprises a sufficient number of zones such that the vascular access vessel can be cannulated at a different zone at least three times per week for four weeks of treatment.

6. The cannulation site selection method as recited claim 1, wherein the vascular access vessel is cannulated to provide access to the vessel for single-needle hemodialysis.

7. A method for rotatable selection of sites for cannulation through skin of a patient for subcutaneous vascular access, the cannulation site selection method comprising steps of:
   subcutaneously implanting an arteriovenous access graft in a body of a patient, the graft including an access region defined by a raised surface on the graft;
   providing a template having an inner surface and an outer surface, the template defining an opening for a plurality of zones, each of the plurality of zones configured for receiving a plurality of simultaneous cannulations accessing the graft;
   marking the outer surface of the template, the marking defining each of the plurality of zones for use as cannulation sites along the graft;
   positioning the template on the skin of the patient adjacent the graft such that the opening aligns with the graft; and
   using the marking for selecting a first zone for a cannulation site into the graft such that the cannulation site in the first zone is spaced from and not adjacent to a second zone used for cannulation immediately previously to the first zone.

8. The cannulation site selection method as recited in claim 7, further comprising a step of cannulating the graft through the skin of the patient at the cannulation site in the first zone.

9. The cannulation site selection method as recited in claim 7, further comprising a step of using the marking for selecting a corresponding third zone fora cannulation site into the graft such that the third zone is spaced from and not adjacent to the first zone used for cannulation immediately previously to the third zone; and
   cannulating the graft through the skin of the patient at the cannulation site in the third zone.

10. The cannulation site selection method as recited in claim 9, further comprising a step of using the marking for selecting a corresponding fourth zone for a cannulation site into the graft such that the fourth zone is spaced from and not adjacent to the third zone used for cannulation immediately previously to the fourth zone; and cannulating the graft through the skin of the patient at the cannulation site in the fourth zone.

11. The cannulation site selection method as recited claim 7, wherein the step of marking the template for defining each of the plurality of zones for use as cannulation sites along the graft comprises a sufficient number of zones such that the graft can be cannulated at a different zone at least three times per week for four weeks.

12. The cannulation site selection method as recited claim 7, wherein the graft is cannulated to provide access to the graft for single-needle hemodialysis.

13. A method for rotatable selection of sites for cannulation through skin of a patient for subcutaneous vascular access, the cannulation site selection method comprising steps of:
  surgically forming an arteriovenous fistula in a body of a patient;
  providing a template having an inner surface and an outer surface, the template defining an opening for a plurality of zones, each of the plurality of zones configured for receiving a plurality of simultaneous cannulations accessing the fistula;
  marking the outer surface of the template, the marking defining each of the plurality of zones for use as cannulation sites along the fistula;
  positioning the template on the skin of the patient adjacent the fistula such that the opening aligns with the fistula; and
  using the marking for selecting a first zone for a cannulation site into the fistula such that the cannulation site in the first zone is spaced from and not adjacent to a second zone used for cannulation immediately previously to the first zone.

14. The cannulation site selection method as recited in claim 13, further comprising a step of cannulating the fistula through the skin of the patient at the cannulation site in the first zone.

15. The cannulation site selection method as recited in claim 13, further comprising a step of using the marking for selecting a corresponding third zone fora cannulation site into the fistula such that the third zone is spaced from and not adjacent to the first zone used for cannulation immediately previously to the third zone; and
  cannulating the fistula through the skin of the patient at the cannulation site in the third zone.

16. The cannulation site selection method as recited in claim 15, further comprising a step of using the marking for selecting a corresponding fourth zone for a cannulation site into the fistula such that the fourth zone is spaced from and not adjacent to the third zone used for cannulation immediately previously to the fourth zone; and
  cannulating the fistula through the skin of the patient at the cannulation site in the fourth zone.

17. The cannulation site selection method as recited claim 13, wherein the step of marking the template for defining each of the plurality of zones for use as cannulation sites along the fistula comprises a sufficient number of zones such that the fistula can be cannulated at a different zone at least three times per week for four weeks.

18. The cannulation site selection method as recited claim 13, wherein the fistula is cannulated to provide access to the fistula for single-needle hemodialysis.

\* \* \* \* \*